United States Patent [19]

Brierley et al.

[11] Patent Number: 4,695,727
[45] Date of Patent: Sep. 22, 1987

[54] OPTICAL ANALYTICAL INSTRUMENT WITH AUTOMATIC SAMPLE CHANGING

[75] Inventors: Philip R. Brierley; Stephen R. Lowry, both of Madison, Wis.

[73] Assignee: Nicolet Instrument Corporation, Madison, Wis.

[21] Appl. No.: 837,608

[22] Filed: Mar. 7, 1986

[51] Int. Cl.⁴ .......................................... G01N 21/35
[52] U.S. Cl. .................................. 250/328; 250/339; 356/244
[58] Field of Search ................ 422/64; 250/328, 341, 250/339; 356/244; 353/117

[56] References Cited

U.S. PATENT DOCUMENTS

| | | |
|---|---|---|
| 3,236,113 | 2/1966 | Robinson et al. . |
| 3,319,370 | 5/1967 | Robinson . |
| 3,655,288 | 4/1972 | Lieberman et al. . |
| 3,887,277 | 6/1975 | Tepper . |
| 3,918,818 | 11/1975 | Giles ..................................... 356/36 |
| 3,951,609 | 4/1976 | Palenscar .............................. 356/72 |
| 3,985,507 | 10/1976 | Litz et al. ............................. 356/244 |
| 4,001,584 | 1/1977 | Mueller et al. ....................... 250/328 |
| 4,001,585 | 1/1977 | Coutarel ............................... 250/328 |
| 4,002,908 | 1/1977 | Coutarel ............................... 250/328 |
| 4,002,909 | 1/1977 | Packard et al. ...................... 250/328 |
| 4,042,303 | 8/1977 | Huber ................................... 356/244 |
| 4,090,848 | 5/1978 | Naono ................................... 356/246 |
| 4,152,390 | 5/1979 | Nosco et al. .......................... 422/63 |
| 4,262,205 | 4/1981 | Abu-Shumays .................. 250/458.1 |
| 4,296,070 | 10/1981 | Montalto et al. ...................... 422/65 |
| 4,349,510 | 9/1982 | Kolemainen et al. ............... 356/244 |
| 4,387,990 | 6/1983 | Yazawa et al. ...................... 356/244 |
| 4,396,287 | 8/1983 | Hildebrand et al. ................ 356/244 |
| 4,444,497 | 4/1984 | Hildebrand et al. ................ 356/244 |
| 4,479,058 | 10/1984 | Gast et al. ............................. 250/343 |
| 4,528,159 | 7/1985 | Liston ................................... 356/244 |
| 4,534,646 | 8/1985 | Tamm et al. ......................... 356/244 |

OTHER PUBLICATIONS

Optical Layouts and Specifications of Nicolet FT-IR Spectrometers, Nicolet Instru. Corp., Madison, Wisc., Mar. 1980.
Nicolet 20DXB/205XB Fourier Transform Infrared Spectrometer Series new product bulletin, undated.

*Primary Examiner*—Carolyn E. Fields
*Attorney, Agent, or Firm*—Isaksen, Lathrop, Esch, Hart & Clark

[57] ABSTRACT

An infrared spectroscopy instrument includes a housing having a sample chamber which is sized and shaped to accommodate the body of an automatic feeding slide projector of the type commonly utilized with standard photographic slide transparencies. The infrared beam is reflected by a system of mirrors into a beam path which extends through a portion of the slide projector mechanism ordinarily occupied by the projector lamp and optics, which have been removed. Samples are held in special sample holders adapted in size and shape to fit the compartments utilized in the slide magazine of the projector. These sample holders are indexed one at a time under the control of the instrument into a viewing position in the path of the infrared beam, and the beam passed through the sample is then collected and focused onto a detector. The feeding apparatus of the projector allows any selected sample holder in the magazine to be indexed into the slide viewing position, and allows automatic computer control of the order in which the samples are analyzed.

9 Claims, 9 Drawing Figures

OPTICAL ANALYTICAL INSTRUMENT WITH AUTOMATIC SAMPLE CHANGING

FIELD OF THE INVENTION

This invention pertains generally to the field of optical analytical instruments as exemplified by infrared spectrometers and to sample holding apparatus therefor.

BACKGROUND ART

In infrared spectrometers, a beam of infrared radiation from a source is directed through a series of mirrors or other focusing elements onto a sample held in a holder. The radiation transmitted through or reflected from the sample is then collected and directed onto a detector. In Fourier Transform Infrared (FTIR) spectroscopy, the output signal from the detector is analyzed with known computer processing techniques to derive information concerning the structure and composition of the sample.

In typical FTIR spectroscopy instruments, a single sample is held in position in a focused infrared beam by a holding fixture. To change a sample, the operator removes the first sample from the holder and inserts the new sample and then initiates a new scan by the instrument. If many different samples are to be analyzed, the procedures involved in changing samples in the instrument result in a substantial waste of the operator's time as well as reducing the available productive operating time of the instrument. Although automatic sample changers are known and used with other types of spectroscopic equipment, automatic sample changers have not commonly been used in FTIR spectroscopy. Because of the relatively limited number of these specialized instruments that are produced, construction of automatic sample changers especially adapted for FTIR spectrometers has not been economically feasible. The automatic sample changing apparatus used in other types of spectroscopy is generally not adaptable to use with FTIR spectrometers because of limitations of space and positioning required with the FTIR instruments. In addition, each manufacturer of present sample changers utilizes a distinct sample holder which is adapted to the particular sample changer made by the manufacturer, limiting the interchangeability of sample holders in different changers. The presently available automatic changers used in general spectroscopy typically have a capacity of about 30 sample holders, are limited to positioning the sample holders sequentially, cannot select a particular sample among the various samples, and are generally not capable of testing a particular sample or samples more than once, if desired.

SUMMARY OF THE INVENTION

In accordance with the present invention, an FTIR optical instrument is provided with a housing having a sample chamber which is sized and shaped to accommodate the body of an automatic feeding slide projector of the type commonly utilized with standard photographic slide transparencies. The infrared analytical radiation in the instrument is reflected by a system of mirrors into a beam path which extends through a portion of the slide projector mechanism ordinarily occupied by the projector lamp and optics, which have been removed to provide an unimpeded path through the projector. A sample is held in a special sample holder which is adapted in size and shape to fit in the compartments ordinarily utilized for standard slides in the magazine of the projector apparatus. These sample holders are indexed one by one by the projector into the path of the infrared beam, and the beam passed through the sample is then collected by a further mirror or mirrors within the instrument and focused upon a detector.

By utilizing a standard slide projector mechanism of the type in which the sample holders are arranged in compartments in a circular magazine, the sample holders within the magazine can be indexed in any desired order to the slide viewing position. Thus, samples can be analyzed out of sequence and a single sample can be analyzed several times before completion of analysis on other samples in the magazine. The standard controls of the slide projector—indexing forward, indexing reverse, and power on and off—are sufficient to allow computer control of the projector to select the desired sample holders in non-sequential order as noted above. The projector apparatus can thus be interfaced to a computer controller which can control the analysis of the samples in the magazine in accordance with the programming of the computer to carry out any desired procedures.

The adaptation of the FTIR optic system to accommodate a standard slide projector as the sample feeding apparatus therefor, and the utilization of such readily available commercial apparatus within the FTIR instrument, greatly enhances the capabilities of the instrument at minimum cost and achieves desired results at less expense than would be required to custom construct automatic sample changing equipment adapted to FTIR spectroscopy.

Further objects, features, and advantages of the invention will be apparent from the following detailed description when taken in conjunction with the accompanying drawings.

DETAILED DESCRIPTION OF THE INVENTION

Figure 1:
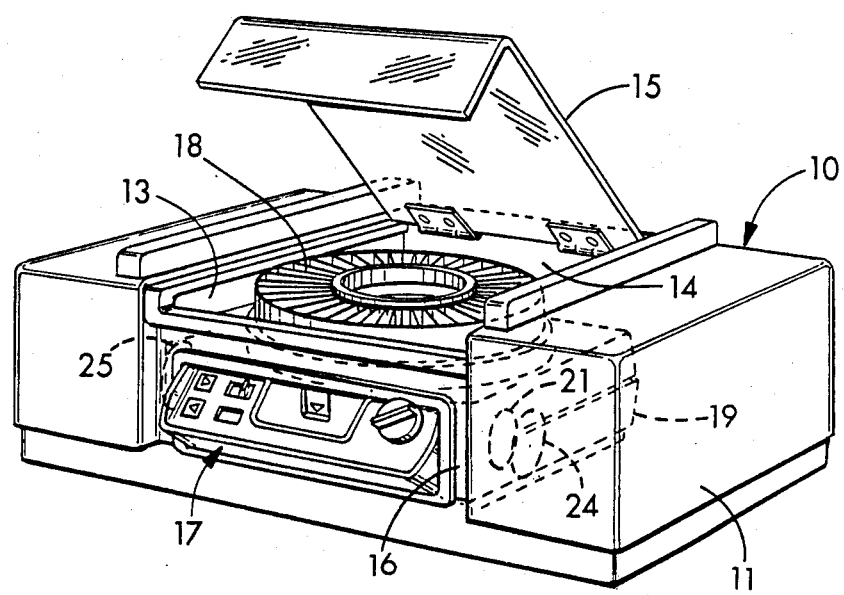
FIG. 1 is an external perspective view showing the analytical instrument of the present invention having automatic sample changing.
Figure 2:
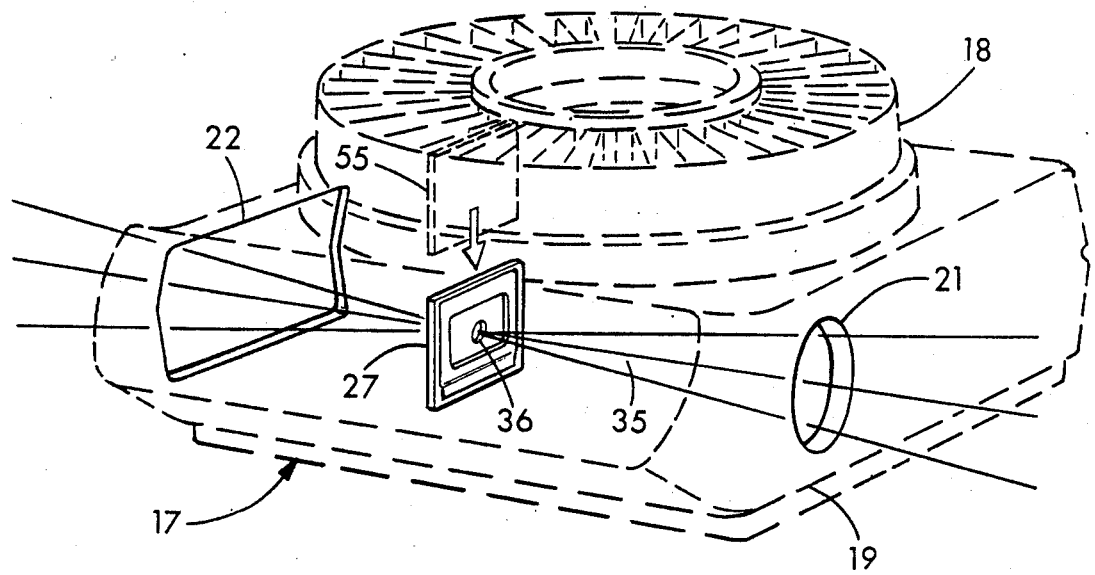
FIG. 2 is a somewhat simplified diagrammatic view showing the operation of the sample changer with respect to the beam of analytical radiation.

With reference to the drawings, an optical analytical instrument having automatic sample changing in accordance with the invention is illustrated in external perspective view at 10 in FIG. 1. The instrument 10 includes a housing 11 which encloses various optical components of the system as well as the interface electronics. Within the housing 11 is a centrally located sample chamber 12 defined by side walls 13, a back wall 14, a cover 15 which may be closed to cover the sample chamber and a front panel 16. Within the sample chamber 12 is mounted a modified slide projector unit 17, preferably of the type that has a slide feeding arrangement in which the slides are carried in a circular magazine 18. In the preferred projector apparatus, any slide in the compartments of the magazine can be indexed into the slide gate position in which the selected slide can be transported to a position (the slide viewing position) in the main body portion 19 of the projection apparatus in which it would be interposed normally in the beam of light from the projection lamp. An example of a commercial slide projector apparatus which may be utilized in the present invention is a Carousel 4200 projector manufactured by the Eastman Kodak Company. The projector 17 has an opening 21 (entrance opening), shown in dashed lines in FIG. 1, through which the beam from the projector would normally be projected. A second opening 22 (exit opening), shown in FIG. 2, is ordinarily covered by a door and normally allows access to the projection lamp. In accordance with the present invention, the lamp assembly and projection lens from the projection unit 17 are removed, creating an unimpeded path for light from the projection opening 21 to the lamp access opening 22. An inlet opening illustrated by the dashed line labeled 24 in FIG. 1 is formed in one side wall 13 of the sample chamber 12 to align with the opening 21 in the projector 17 when it is situated within the sample chamber, and an outlet opening 25 is formed in the other side wall 13 of the sample chamber 12 which aligns with the opening 22 in the projector 17 when the projector rests in its position within the sample chamber. In accordance with the present invention, the sample chamber is formed with the walls 13, 14 and 16 defining a generally rectangular chamber which is sized to accommodate the generally rectangular, standard-type projectors exemplified by the projector 17 (e.g., preferably about one-half inch clearance between the walls and the sides of the projector body 19), while restraining the position of the projector such that the openings 24 and 25 in the walls of the sample chamber line up with the projector openings 21 and 22, respectively. For example, as shown in FIG. 1, the front panel wall 16 may be formed as an open frame which is adapted to surround the extending control panel of the projector 17 so that the projector is accurately located in its proper position when the projector control panel is inserted in the open frame. In addition, recesses 26 may be formed in the floor of the sample chamber into which the foot pads (not shown) of the projector will fit. With the projector properly located, an infrared beam can pass unimpeded and be focused upon a sample holder 27 in the slide viewing position, i.e., generally at the center of the projector apparatus 17 and generally at the center of the width of the sample chamber 12.

Figure 3:
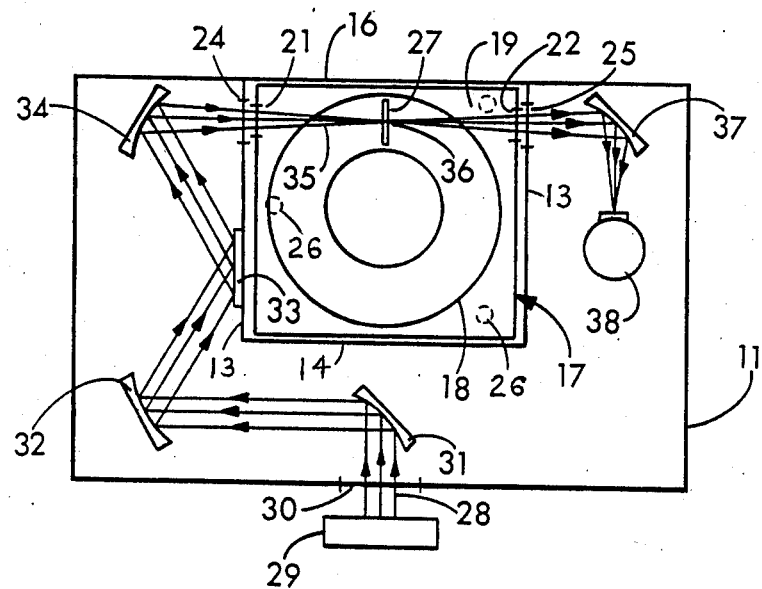
FIG. 3 is a simplified top plan view of the instrument of the present invention illustrating the path of infrared radiation therein.

The relative position of the projector apparatus 17 within the sample chamber 12 is illustrated schematically in FIG. 3. A beam 28 of infrared radiation, preferably collimated, from a source 29 passes through an opening 30 in the back wall of the case 11 and impinges upon a first flat mirror 31 which reflects the beam to a second flat mirror 32. The collimated beam is reflected from the mirror 32 to a third flat mirror 33 and thence to a parabolic focusing mirror 34. The mirror 34 directs the beam in a path 35 defined between the inlet opening 24 and outlet opening 25 and focuses the beam onto a focal plane preferably located at the position of the center of a sample holder 27 held in the slide viewing position within the projector 17. As illustrated, the converging beam 35 reflected from the mirror 34 passes through the opening 24 in the wall 13 of the sample chamber and through the opening 21 in the projector before converging onto the sample 36 held within the holder 27. After passing through a sample 36 at the center of holder 27, the diverging transmitted beam passes through the openings 22 and 25 and impinges upon a parabolic focusing mirror 37 which focuses the beam onto a detector 38. As best illustrated in FIG. 3, the spacing between the side walls 13 is sufficient to accommodate the width of the base 19 of the projector 17 but, along with the front panel frame 16 and the foot pad recesses 26, positively locates the projector so that the focused beam reflected from the mirror 34 will focus at a focal plane located at the position of the sample holder 27 which has been transported downwardly from the magazine into the beam path 35 by the projection apparatus 17. Similarly, the spacing between the rear wall 14 of the sample chamber and the front panel 16 accommodates the front to back width of the base 19 of the projector but the engagement of the front control panel of the projector with the front panel 16 restricts the position of the projector so that the focused beam from the mirror 34 strikes the center of the sample holder 27 in the viewing position. The height of the chamber 12 is greater than the height of the projector apparatus 17 so that the cover 15 can be closed without interference.

Figure 4:
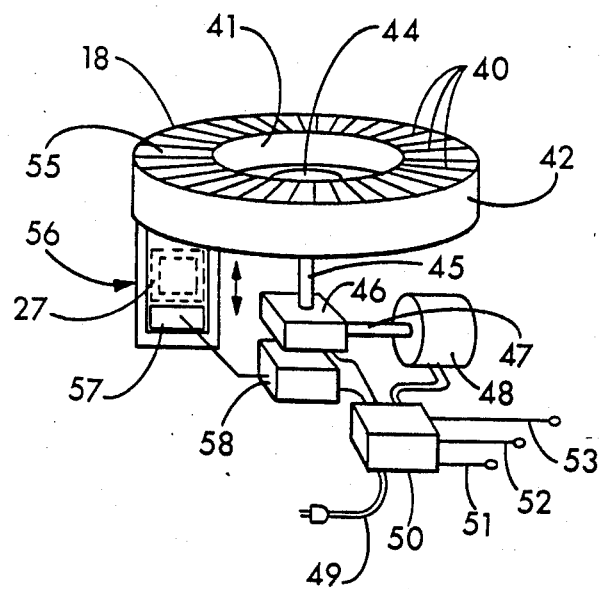
FIG. 4 is an illustrative view showing the relative arrangement of the various parts of the sample feeding mechanism of the invention.

The sample holder feeding mechanism within the projector 17 is of standard design, with the pertinent parts thereof shown in simplified schematic form in FIG. 4 for illustration of the transport of the sample holder from the magazine to the viewing position. Such slide projector operating mechanisms are described, for example, in U.S. Pat. Nos. 3,236,113, 3,319,370, and 3,887,277. The circular magazine 18 has numerous radially arranged slots or compartments defined by radially extending walls 40 and inner and outer cylindrical peripheral walls 41 and 42. The magazine 18 also has a central hub 44 which is formed to connect to a drive shaft 45 which extends to a drive engagement mechanism 46. The mechanism 46 receives power from the shaft 47 of a drive motor 48 which, when energized, rotates the shaft 47 and which may simultaneously drive a fan (not shown). The drive engagement mechanism 46 and the drive motor 48 are controlled by an electrical control circuit 50 receiving power from a line 49 and having remote input forward and reverse control lines 51 and 52 and a common power line 53. Connection of the power line 53 to the line 51 or 52 causes the engagement mechanism to transmit power from the shaft 47 to the drive shaft 45 to rotate the magazine 18 one compartment forward or backward, respectively. The sample holder in the particular compartment 55 which is located over the viewing position 56 can be engaged by a slide transport elevator 57 which engages the sample holder at its bottom and can be retracted to a downward position by a slide engagement driver 58 to drop the sample holder to the viewing position 56.

Figure 5:
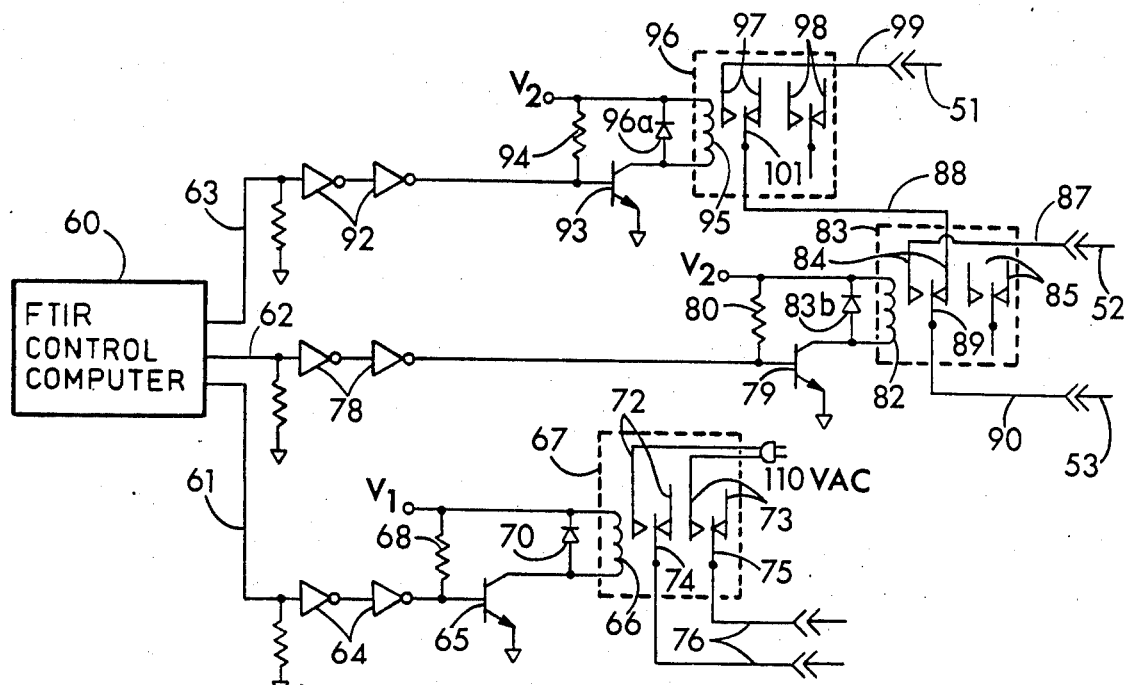
FIG. 5 is an electrical schematic diagram illustrating a circuit within the instrument of FIG. 1 for interfacing a computer control system with the electrical controls of the sample feeding mechanism of the instrument.

In the normal slide changing sequence for such projectors, the sample holder 27 which is in the viewing position 56 is driven upwardly into the empty compartment 55 by action of the slide engagement drive 58 pushing the elevator 57 upwardly. The drive engagement mechanism 46 then rotates the magazine 18 one slot forward or backward, as commanded by the signals on the lines 51–53. When the indexing of the magazine one slot has occurred, the slide engagement drive mechanism is then operated again to drop the elevator 57 downwardly, thereby drawing downwardly the sample holder which is now in the position 55. Upon application of a control signal to index the magazine one more slot, the drive engagement mechanism 58 again presses the elevator 57 upwardly to drive the sample holder 27 contained therein back into the empty slot at the location 55, whereupon the drive engagement mechanism 46 is activated to index the magazine 18 one more slot forward or backward. The slots of the magazine 18 (e.g., 80 slots or compartments for a typical low density tray, 140 slots for a typical high density tray) are numbered and can be initially positioned by the operator so that the initial slot occupies the position 55. The operator can therefore provide control signals to the projector apparatus 17 to rotate the magazine 18 a selected number of slots so that a particular sample holder containing a desired sample can be indexed into the position 55. The operator will know the location of the slot at the position 55 by counting the number of pulses provided to the projection apparatus to rotate it one slot. Similarly, the computer system which controls the FTIR apparatus can be automatically programmed to control the projection apparatus. As long as the magazine is initially positioned with the first numbered or initial position slot at the position 55, the computer can keep track of the slot which is at the position 55 by counting the number of times that the magazine has been rotated one slot at a time either backward or forward. An electrical circuit for interfacing an FTIR spectrometer control computer with the controls of the projector apparatus 17 is shown in schematic form in FIG. 5. Signals from the FTIR control computer 60 can include output signals on a line 61 to turn the projection apparatus on or off, on a line 62 to index the apparatus backward one slot, and on a line 63 to index the apparatus forward one slot. The output signal on the line 61 is passed through a pair of buffer amplifiers 64 to the base of a bipolar transistor 65. The coil 66 of a relay unit 67 is connected between a source of positive voltage $V_1$ and the collector of the transistor 65, with the emitter of the transistor connected to common return. Bias voltage is provided to the base 65 from the voltage $V_1$ through a bias resistor 68 and a diode 70 is connected across the coil 66 to shunt current from the coil during switching. The relay 67 may be of the type shown, having a double pole, single throw arrangement with pair of relay contact 72 and 73, one of the contacts in each pair of contacts 72 and 73 being connected to a source of AC line voltage with the other contacts left open. The relay contact switches 74 and 75, which are switched by the action of the coil 66, are connected to a receptacle 76 into which the power plug 49 of the projection apparatus 17 may be inserted.

In a similar manner, the output signal on the line 62 is passed through a pair of buffer amplifiers 78 and thence to the base of a bipolar transistor 79. The base of the transistor 79 is also connected to a source of voltage $V_2$ through a biasing resistor 80. A relay coil 82 of a relay unit 83 is connected between the voltage $V_2$ and the collector of the transistor 79, and the emitter of the transistor is connected to common return. A shunt diode 83b is connected across the relay coil 82. The relay 83 also has two pairs of contacts 84 and 85, with the contacts 85 being left unconnected. One of the contacts in the pair 84 is connected to an output terminal 87 which extends to the reverse input line 52 of the projector apparatus 17 while the other of the contacts in the pair 84 is connected to a line 88. One movable contact switch 89 in the relay is connected to a line 90 which may be connected to the common power line 53 from the projector apparatus 17. Thus, when the coil 82 is activated, the switch 89 will move to the position engaging the contact 87 to provide continuity between the lines 90 and 87, thereby driving the projection apparatus in reverse.

An output pulse on the line 63 from the control computer 60 is provided through a pair of isolation amplifiers 92 to the base of a bipolar transistor 93 which receives a bias voltage from a supply voltage $V_2$ through a bias resistor 94. A relay coil 95 of a relay unit 96 is connected between the voltage $V_2$ and the collector of the transistor 93, and the emitter of the transistor 93 is connected to common return. A shunt diode 96a is connected across the coil 95. The relay 96 also has a first pair of relay contacts 97 and a second pair 98 which are left unconnected. One of the contacts in the pair 97 is connected to a line 99 leading to the forward input line 51 of the projector apparatus 17 while the other contact is left open. The movable switch 101 of the relay is connected to the line 88 from the relay 83 and in the normal or unenergized condition of the coil 95 touches the one of the pair of contacts 97 which is open. When the coil 95 is energized, the switch 101 switches to the position engaging the contact connected to the line 99, thereby providing electrical power from the line 90 through the switch 89 to the line 88 and thence through the contact 97 to the line 99.

Figure 6A:
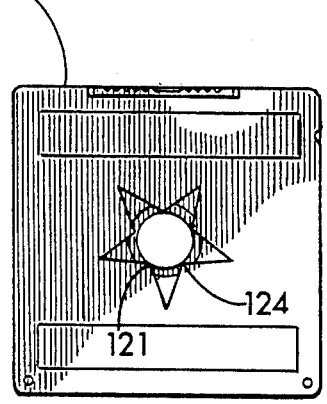
FIGS. 6A–6D illustrate a sample holder formed in accordance with the present invention which is adapted to hold samples to be analyzed and to be accommodated in compartments within a standard slide projector magazine.
Figure 6B:
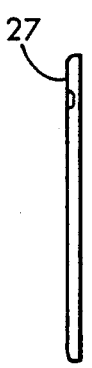
Figure 6C:
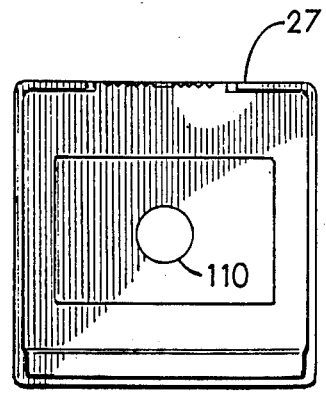
Figure 6D:
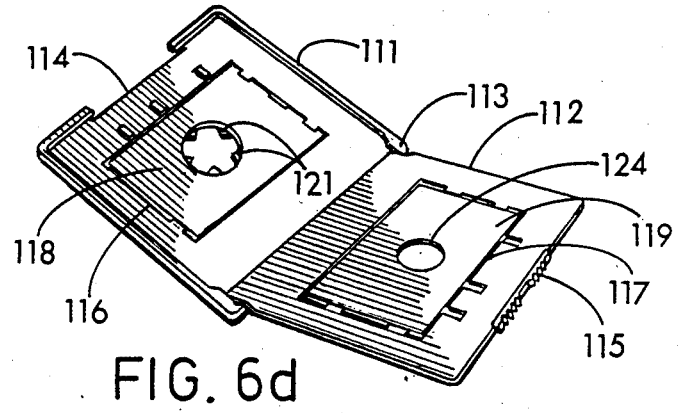

A sample holder 27 in accordance with the present invention is illustrated in the views of FIGS. 6A–6D. The sample holder 27 is shaped and sized to conform substantially to a standard slide projector slide holder, typically of the type that is adapted to hold 35 millimeter film transparencies. Specifically, the slide holder 27 is formed of light-weight plastic approximately 5 centimeters by 5 centimeters on a side (about 2 inches by 2 inches) and approximately 2 to 3 millimeters thick, as illustrated in FIG. 6B. The sample holder 27 has a central opening 110 onto which the infrared beam is focused and in which the sample to be analyzed will be positioned. To hold the sample in position, the sample holder preferably comprises a modification of an ordinary film slide holder, as illustrated in FIG. 6D, having two half parts 111 and 112 which are joined together at a hinge 113 and which interlock when closed by an interlocking extension 114 on one of the halves 111 which mates with a corresponding indentation 115 on the other half 112. In an ordinary slide holder, the two halves 111 and 112 would have openings generally as defined by the lines 116 and 117 of rectangular arrangement which would approximately define the boundaries of the viewing area of a transparent film element which would be held in the slide element. However, in the sample holder of the present invention, the areas 116 and 117 are occupied by special panels 118 and 119 which snap into place in the openings 116 and 117 and which have central opening portions therein to define the open area 110 through which the infrared beam may pass. Specifically, it is preferred that the panels 118 and 119 include means thereon, such as the extending flexible plastic projections 121 on the panel 118, which can cooperate to resiliently hold a specimen to be analyzed between the panels 118 and 119. For a sample of a relatively small thickness and large lateral size, the additional holding elements 121 may not be necessary and the resilience of the thin panels 118 and 119 may be sufficient to hold the sample in place. However, for smaller samples or those of greater thickness in which it is preferred to utilize a smaller piece of sample material, the projections 121 are positioned and sized so that they will fit over the position of the inner opening 124 in the panel 119, as illustrated in the front view of FIG. 6A, to best hold the sample in position.

It is understood that the invention is not confined to the particular embodiments described herein as illustrative, but embraces such forms thereof as come within the scope of the following claims.

What is claimed is:

1. An anlaytical instrument for use in infrared spectroscopy comprising:
   (a) a housing with walls therein defining a sample chamber, including a wall on one side of the chamber having an inlet opening therein and a wall on the other side of the chamber having an outlet opening therein, a beam path being defined between the inlet and outlet openings within the sample chamber;
   (b) an infrared detector and optical elements within the housing arranged to receive an incoming beam of infrared radiation from a source and to direct the beam of radiation across the beam path between the inlet and outlet openings in the sample chamber walls and onto the detector;
   (c) slide projector apparatus having a magazine adapted to hold a plurality of sample holders each having substantially the dimensions of a photometric transparency slide with which the slide projector apparatus is adapted to be used, and further including means therein for selectively transporting a single sample holder at a time from the magazine to a slide viewing position away from the magazine, the projector apparatus being free of obstructions in an optical path therethrough which extends from an entrance opening to an exit opening in the projector apparatus and which includes the slide viewing position; and
   (d) means for mounting the projector apparatus within the sample chamber of the housing such that the projector apparatus is located with the slide viewing position interposed in the beam path and with the beam path passing unimpeded through the projector apparatus.

2. The instrument of claim 1 wherein the projector apparatus is of the type having a circular magazine adapted to hold standard photographic transparency slides, wherein said magazine comprises means to hold infrared sample holders of a size substantially matching the size of standard slides, and wherein means is responsive to control signals selectively index the magazine forwardly and backwardly to transport one sample holder at a time from the magazine into the slide viewing position.

3. The instrument of claim 1 wherein the optical elements comprise means for focusing the infrared beam in the beam focusing path in the sample chamber at a focal plane which substantially coincides with the slide viewing position of the projector apparatus.

4. The instrument of claim 1 including a plurality of sample holders mounted in the slide holding magazine of the projector apparatus, each sample holder formed of two rectangular half portions hingedly connected together, the half portions having openings at the centers thereof to allow passage of a beam of infrared radiation therethrough and further including means thereon for engaging and holding a sample to be analyzed in position within the openings in each half portion when the two half portions are closed together.

5. The instrument of claim 2 including means for providing control signals to the projector apparatus to cause the same to transfer a selected one of a plurality of sample holders held in the slide holding slots of the slide magazine into the sample holding position.

6. The instrument of claim 1 wherein the optical elements within the housing include a plurality of mirrors positioned to intercept a collimated beam of infrared radiation from a source and transmitted through an optical path within the housing around the sample chamber and a focusing mirror onto which the collimated beam is incident which focuses the beam and transmits it through the inlet opening of the sample chamber to focus the beam substantially at the slide viewing position within the projector apparatus, and further including a second focusing mirror positioned to receive the infrared radiation passed through a sample at the slide viewing position and transmitted through the outlet opening from the sample chamber and to focus the beam so received onto the detector.

7. An analytical instrument for use in infrared spectroscopy comprising:
   (a) a housing with walls therein defining a sample chamber, including a wall on one side of the chamber having an inlet opening therein and a wall on the other side of the chamber having an outlet opening therein, a beam path being defined between the inlet and outlet openings within the sample chamber;
   (b) an infrared detector and optical elements within the housing arranged to receive an incoming beam of infrared radiation from a source and to direct the beam of radiation across the beam path between the inlet and outlet openings in the sample chamber walls and onto the detector;
   (c) slide projector apparatus having a circular magazine adapted to hold a plurality of sample holders each having substantially the dimensions of a photographic transparency slide with which the slide projector apparatus is adapted to be used, and further including means therein for selectively transporting a single sample holder at a time from the magazine to a slide viewing position away from the magazine, the projector apparatus being free of obstructions in an optical path therethrough which extends from an entrance opening to an exit opening in the projector apparatus and which includes the slide viewing position, and wherein means responsive to control signals selectively index the magazine forwardly and backwardly to transport one sample holder at a time from the magazine into the slide viewing position;
   (d) means for mounting the slide projector apparatus within the sample chamber such that the projector apparatus is located with the slide viewing position interposed in the beam path and with the beam path passing unimpeded through the projector apparatus; and (e) control means, connected to provide control signals to the projector apparatus, for determining the identification of the compartment holding a particular sample holder which is over the slide holding position and for providing control signals to the projector apparatus to cause the same to transfer a selected one of the plurality of sample holders held in the slide magazine into the sample holding position.

8. The instrument of claim 7 wherein the optical elements comprise means for focusing the infrared beam in the beam focusing path in the sample chamber at a focal plane which substantially coincides with the slide viewing position of the projector apparatus.

9. The instrument of claim 8 including a plurality of sample holders mounted in the slide holding magazine of the projector apparatus, each sample holder formed of two rectangular half portions hingedly connected together, the half portions having openings at the centers thereof to allow passage of a beam of infrared radiation therethrough and further including means thereon for engaging and holding a sample to be analyzed in position within the openings in each half portion when the two half portions are closed together.

* * * * *